United States Patent
Thawani et al.

(10) Patent No.: US 11,433,435 B2
(45) Date of Patent: Sep. 6, 2022

(54) APPARATUS AND METHODS FOR IMPROVING CATHETER FUNCTION

(71) Applicant: The Trustees of the University of Pennsylvania, Philadelphia, PA (US)

(72) Inventors: Jayesh P. Thawani, Philadelphia, PA (US); Jared M. Pisapia, Philadelphia, PA (US); Hongjie Zhu, Austin, TX (US); M. Sean Grady, Philadelphia, PA (US); Andrew Tsourkas, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 385 days.

(21) Appl. No.: 15/769,388

(22) PCT Filed: Oct. 18, 2016

(86) PCT No.: PCT/US2016/057495
§ 371 (c)(1),
(2) Date: Apr. 19, 2018

(87) PCT Pub. No.: WO2017/070095
PCT Pub. Date: Apr. 27, 2017

(65) Prior Publication Data
US 2018/0281028 A1 Oct. 4, 2018

Related U.S. Application Data

(60) Provisional application No. 62/397,603, filed on Sep. 21, 2016, provisional application No. 62/243,285, filed on Oct. 19, 2015.

(51) Int. Cl.
*B08B 3/12* (2006.01)
*B08B 7/02* (2006.01)
(Continued)

(52) U.S. Cl.
CPC .................... *B08B 3/12* (2013.01);
*A61L 2/02* (2013.01); *A61L 2/03* (2013.01);
*A61M 25/00* (2013.01);
(Continued)

(58) Field of Classification Search
CPC ......... B08B 3/12; B08B 7/028; B08B 9/0326; A61L 2/02; A61L 2/03; A61M 25/00;
(Continued)

(56) References Cited

U.S. PATENT DOCUMENTS 3,640,295 A 2/1972 Peterson
4,698,058 A 10/1987 Greenfeld et al.
(Continued)

FOREIGN PATENT DOCUMENTS

| DE | 4432683 A1 * | 3/1996 | ......... G02B 27/0006 |
| EP | 1197177 A2 * | 4/2002 | ............. A61B 1/122 |
| WO | WO-2006031106 A1 * | 3/2006 | ............... A61L 2/02 |

OTHER PUBLICATIONS

International Preliminary Report on Patentability for International Application No. PCT/US2016/057495, dated Apr. 24, 2018—8 pages.
(Continued)

*Primary Examiner* — Alexander Markoff
(74) *Attorney, Agent, or Firm* — Baker Botts L.L.P.

(57) ABSTRACT

An ultrasonication apparatus is provided for improving catheter function. The ultrasonication apparatus includes a transducer configured to produce ultrasonic waves for ultrasonication and a chamber for containing a fluid having a passage for receiving a catheter. The chamber is adapted to receive the ultrasonic waves from the transducer.

12 Claims, 11 Drawing Sheets

(51) Int. Cl.
*A61M 25/00* (2006.01)
*A61L 2/02* (2006.01)
*A61L 2/03* (2006.01)
*B08B 9/032* (2006.01)

(52) U.S. Cl.
CPC ..... *B08B 7/028* (2013.01); *A61M 2025/0019* (2013.01); *A61M 2209/082* (2013.01); *A61M 2209/10* (2013.01); *B08B 9/0326* (2013.01)

(58) Field of Classification Search
CPC .... A61M 2025/0019; A61M 2209/082; A61M 2209/10
See application file for complete search history.

(56) References Cited

U.S. PATENT DOCUMENTS

| | | | |
|---|---|---|---|
| 4,710,233 A | 12/1987 | Hohmann et al. | |
| 4,903,718 A | 2/1990 | Sullivan | |
| 5,865,199 A | 2/1999 | Pedziwiatr et al. | |
| 6,494,222 B1* | 12/2002 | Mitsumori | B08B 3/006 134/184 |
| 8,709,338 B2 | 4/2014 | Bates et al. | |
| 11,191,886 B2* | 12/2021 | Karimov | A61M 25/02 |
| 2002/0017316 A1* | 2/2002 | Ochiai | A61B 1/123 134/102.1 |
| 2005/0028376 A1* | 2/2005 | Stones | B27G 19/003 30/381 |
| 2005/0220665 A1* | 10/2005 | Ding | A61L 2/186 422/20 |
| 2007/0244423 A1* | 10/2007 | Zumeris | A61M 25/0017 604/22 |
| 2008/0047575 A1 | 2/2008 | Puskas | |
| 2008/0289971 A1* | 11/2008 | Shigihara | A61L 2/202 205/687 |
| 2009/0241987 A1* | 10/2009 | Serizawa | A61L 2/18 134/1 |
| 2011/0132404 A1* | 6/2011 | Lutz | A61L 2/18 134/34 |
| 2013/0146108 A1* | 6/2013 | Suzuki | A61B 1/123 134/113 |
| 2013/0186428 A1* | 7/2013 | Lutz | A61L 2/24 134/1 |
| 2014/0163382 A1* | 6/2014 | Gubbini | A61B 8/4455 600/461 |
| 2014/0166059 A1* | 6/2014 | Kosugi | A61L 2/18 134/113 |
| 2016/0000310 A1* | 1/2016 | Takazawa | B08B 3/08 134/200 |
| 2017/0225205 A1* | 8/2017 | Wellens | B08B 3/10 |

OTHER PUBLICATIONS

International Search Report and Written Opinion for International Application No. PCT/US2016/057495, dated Dec. 23, 2016—8 pages.

* cited by examiner

APPARATUS AND METHODS FOR IMPROVING CATHETER FUNCTION

CROSS REFERENCE TO RELATED APPLICATIONS

This application is a U.S. National Phase filing of International Application PCT/US2016/057495, filed Oct. 18, 2016, and claims priority to U.S. Provisional Patent Application No. 62/243,285, filed Oct. 19, 2015, and U.S. Provisional Patent Application No. 62/397,603, filed Sep. 21, 2016, the contents of each of which are incorporated herein by reference in their entirety.

FIELD OF THE INVENTION

This disclosure relates to apparatuses for improving catheter function as well as methods for using the same

BACKGROUND OF THE INVENTION

Catheters are used in various medical procedures to facilitate the removal or delivery of fluids from portions of patient's body. When catheters are used to drain bodily fluids or excrement, such catheters are prone to obstructions.

As an example, external ventricular drain (EVD) catheters are widely used in neurosurgery to treat a variety of conditions. These catheters mediate drainage of cerebrospinal fluid (CSF), measure intracranial pressure, provide a conduit through which intrathecal drugs (antibiotics, etc.) can be delivered, and provide a means of sampling CSF. These EVD catheters drain outside the body into reservoir containers at the bedside. When an EVD catheter becomes obstructed by hardened or solidified bodily fluids, the EVD catheter is typically accessed with needle syringes using sterile technique and flushed to remove the obstruction. However, the frequency with which EVD catheters are flushed or accessed is closely related to the risk of EVD-associated infection and ventriculitis (infection of the ventricles). Infections associated with EVDs are notoriously difficult to treat and are associated with significant morbidity and mortality.

As another example, chronic indwelling urinary catheters are placed primarily in elderly patients with voiding dysfunction and those with other physiologic conditions requiring diversion of urine from the bladder. Urinary indwelling catheters may become obstructed with bodily fluids/by-products, e.g., blood or other urinary deposits, requiring flushing or placement of a new device. The risk of infection is increased with accessing the urinary catheters. Although urinary infections vary in terms of severity, urinary infections can lead to life-threatening sepsis. Further, based on data obtained from nursing homes, greater than 100,000 individuals in the United States use chronic indwelling urinary catheters. Up to 50% of patients with these devices will experience catheter encrustation and blockage.

SUMMARY OF THE INVENTION

Aspects of the invention relate to apparatuses for improving catheter function as well as methods for using the same.

In accordance with one aspect of the invention, a first method is provided for improving catheter function. The method includes the steps of positioning a catheter within a chamber, the chamber configured to contain a fluid. The method further includes applying ultrasonic waves produced by a transducer for ultrasonication. The transducer being coupled to the chamber to provide the fluid of the chamber with the ultrasonic waves. Additionally, the method includes eliminating obstructions in the catheter by ultrasonication produced by the ultrasonic waves of the transducer.

In accordance with another aspect of the invention, a first ultrasonication apparatus is provided for improving catheter function. The ultrasonication apparatus includes a transducer configured to produce ultrasonic waves for ultrasonication and a chamber for containing a fluid having a passage for receiving a catheter. The chamber is adapted to receive the ultrasonic waves from the transducer.

In accordance with a further aspect of the invention, a second method is provided for improving catheter function. The method includes the steps of positioning a segment of a catheter within a receptacle in sonic communication with a transducer; applying ultrasonic waves produced by the transducer to the catheter; and eliminating or degrading obstructions in the catheter by ultrasonication produced by the ultrasonic waves of the transducer.

In accordance with an additional aspect of the invention, a second ultrasonication apparatus includes a transducer configured to produce ultrasonic waves directed toward a receptacle for dislodging an obstruction within a segment of a catheter. The receptacle is configured to receive the segment of the catheter.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

The inventors recognized that obstructions in catheters may result in physiologic derangements (for example, increasing intracranial pressure in the case of EVDs, formation of bacterial biofilms in urinary catheters), catheter failure, and retrograde flow. The obstructed catheters may necessitate further manipulations—such as flushing the catheter from the inside. These procedures expose the intraluminal components to infectious agents from the outside environment. Furthermore, obstructed catheters may require replacement in the form of additional medical or surgical procedures.

The inventors further recognized that by developing an ultrasonication apparatus configured to transmit ultrasonic energy into the lumen of a catheter from the outside, complications associated with blocked or occluded catheters may be safely minimized. The inventors further recognized that advantageously, the aforementioned ultrasonication apparatus could be used periodically in order to minimize the adherence and formation of obstructions within catheter or may be used after the formation of an obstruction to eliminate said obstruction from the catheter.

Referring to the figures generally, ultrasonication apparatus 100 may be used ex-ante to reduce the build-up or likelihood of obstructions or ex-post to eliminate obstructions in the catheter system. Additionally or alternatively, ultrasonication apparatus 100 may be handheld. Preferably, ultrasonication apparatus 100 is configured for use with obstructions and/or bodily fluid that is to be discarded. In one embodiment, ultrasonication apparatus 100 is not for use inside the body (e.g., catheter segments inside the body) or for fluids that will be recirculated back into the body.

Figure 1:
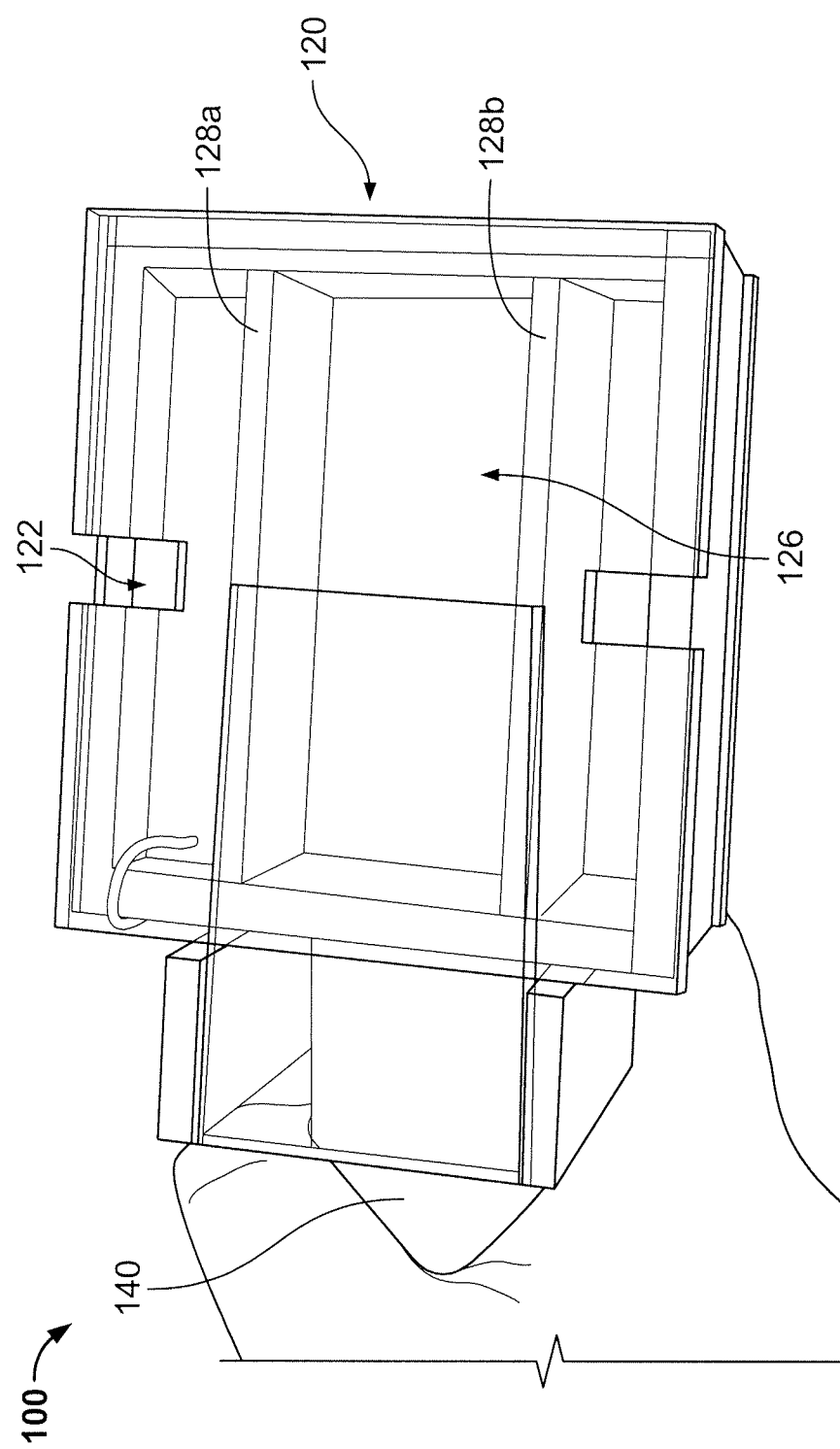
FIG. 1 is a top-view of a first embodiment of an ultrasonication apparatus for improving catheter function in accordance with aspects of the present invention.
Figure 2:
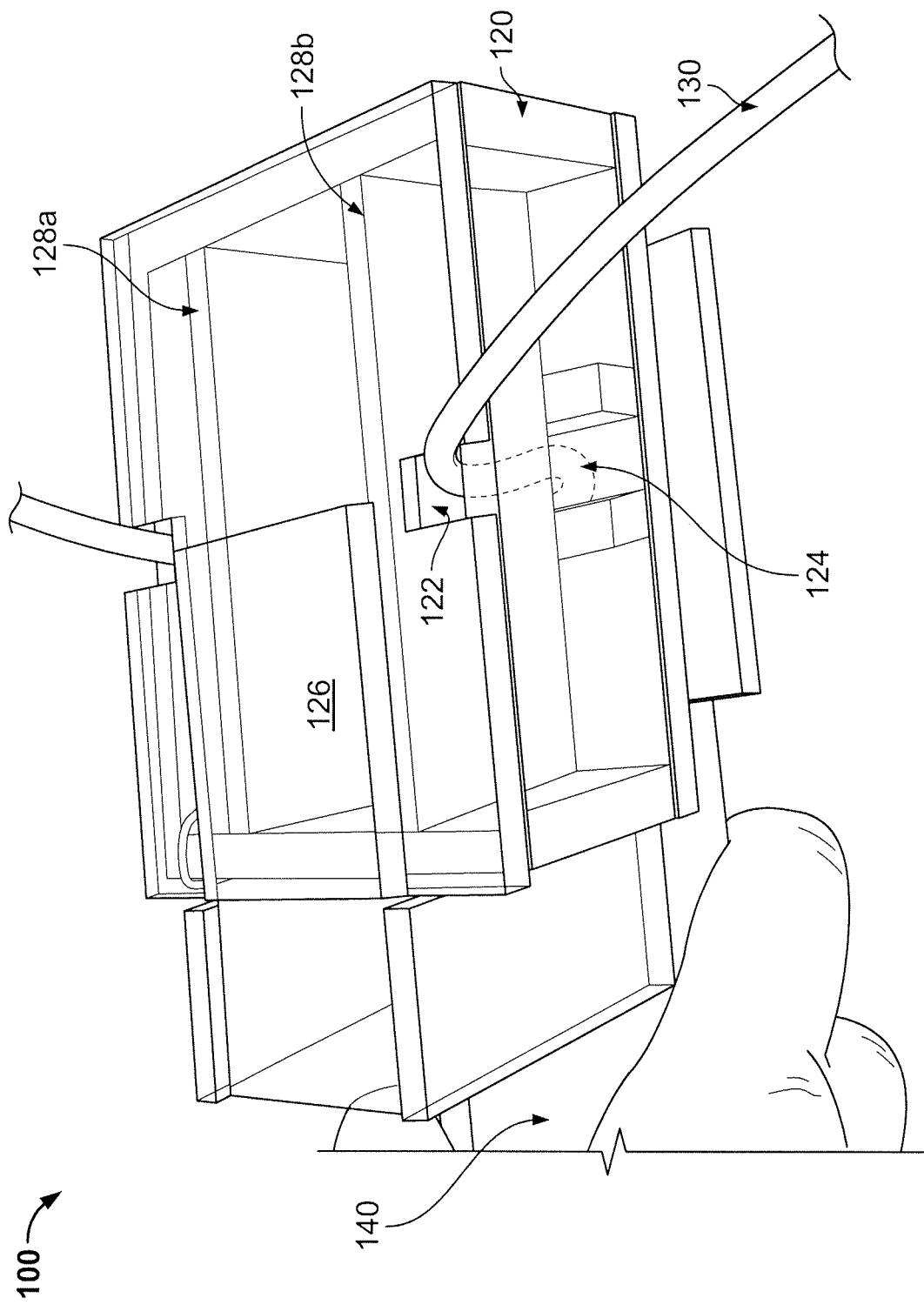
FIG. 2 is a top-view of an ultrasonication apparatus with a segment of a catheter residing therein according to aspects of the present invention.
Figure 3:
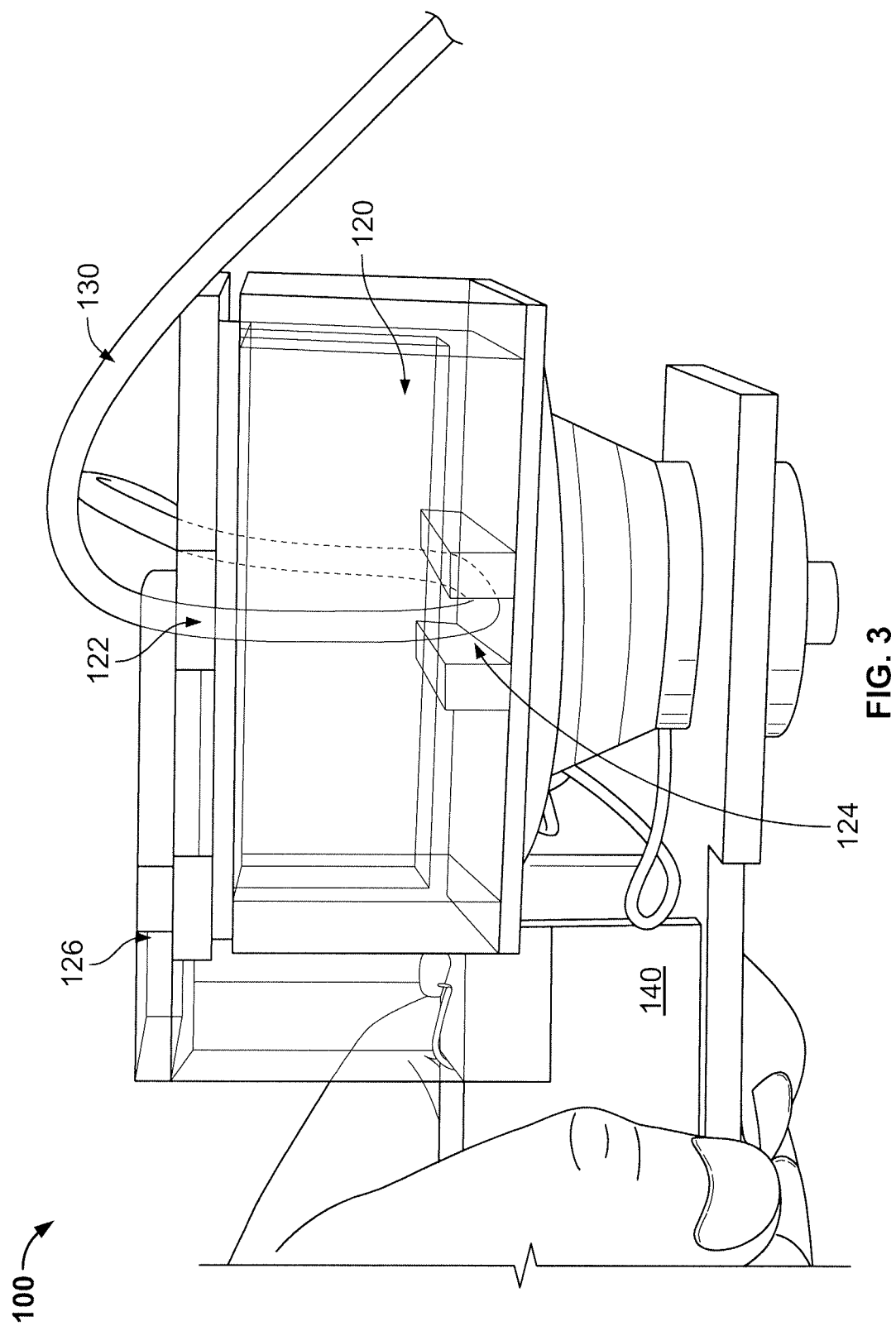
FIG. 3 is a side-view of the ultrasonication apparatus and catheter of FIG. 2.

FIGS. 1-3 illustrate an ultrasonication apparatus 100, which may be employed for improving catheter function. As a general overview, ultrasonication apparatus 100 includes a transducer 110 and a chamber 120 that may be adapted to receive a catheter 130.

Transducer 110 is configured to produce ultrasonic waves for ultrasonication. In one embodiment, the ultrasonic waves have an ultrasonic frequency. The transducer 110 may be coupled to a circuit/generator that can be plugged into a typical electrical outlet. Alternatively or additionally, the transducer 110 may have a circuit/generator integrated into the transducer 110 or be configured to have the capabilities of a circuit/generator. The circuit/generator may facilitate the generation of ultrasonic waves via the transducer 110 at various frequencies including, e.g., frequencies between 1,000 Hz and 1,000,000 Hz; 1,000 Hz and 100,000 Hz; and/or 500 Hz and 10,000 Hz, Preferably, the ultrasonic waves are configured to eliminate obstructions in the catheter 130. In one embodiment, the transducer 110 produces ultrasonic waves approximately at or at a frequency of 40 kilo-Hertz (kHz). In another embodiment, the transducer 110 produces ultrasonic waves approximately at or at a frequency of 28 kHz. In yet a further embodiment, the transducer 110 produces ultrasonic waves approximately at or at a frequency of 60 kHz.

Preferably, the transducer 110 is configured to minimize standing waves. The transducer 110 may employ a sweep function to vary the frequency of the ultrasonic waves, thereby minimizing standing waves. The sweep function modifies the frequency of the ultrasonic waves for a variation of, e.g., 5% or less. In one embodiment, the transducer 110 pulses the ultrasonic waves to increase the rate of elimination of the obstruction. In another embodiment, transducer 110 produces harmonic frequencies for the ultrasonic wave, e.g., using square waves, thereby enabling multiple frequencies to be employed for the ultrasonic waves.

The ultrasonication apparatus 100 also includes a chamber 120 for containing a fluid. The chamber 120 is adapted to receive the ultrasonic waves from transducer 110, For example, chamber 120 may be attached and/or coupled to the transducer 110 such that ultrasonic waves from the transducer 110 are received by the chamber 120, Although chamber 120 is adjacent to transducer 110 in FIGS. 1-3, in one embodiment, chamber 120 is separated from transducer 110, e.g., by one or more pieces of material that are conducive to sound travel.

Chamber 120 has a passage 122 for receiving a catheter 130 or a segment thereof. Passage 122 may generally be located anywhere on chamber 120. In one embodiment, passage 122 is located on cover 126, thereby facilitating the receipt of catheter 130 by chamber 120 with minimal spillage of the fluid contained therein. Cover 126 may be affixed to chamber 120 in any suitable manner. Chamber 120 may also include slots 124 configured to guide the catheter 130 within the chamber 120. One or more submerging walls 128 may extend from cover 126. As cover 126 is moved towards the closed position, thereby encapsulating the fluid contained within chamber 120, the submerging walls 128 may contact and position the catheter 130 into a desired position. In one embodiment, the submerging walls 128 position catheter 130 into slots 124, thereby positioning catheter 130 in a location optimal for receiving the ultrasonic waves from transducer 110.

Ultrasonication apparatus 100 may utilize various sizes, geometries, and types of catheters 130. The dimensions of passage 122 within chamber 120 may be enlarged or made smaller to accommodate various sizes of catheter 130. The distance of submerging walls 128 from the bottom of chamber 120 may be varied to accommodate the outer diameter of catheter 130. Slots 124 may similarly be placed at a distance within chamber 120 to accommodate various outer diameter sizes for catheter 130. The energy of the ultrasonic waves produced by transducer 110 and received by the contents of chamber 120, e.g. the lumen of catheter 130 or substances therein, may be altered by the fluid contained within chamber 120 based on the speed that sound may travel through said fluid and the catheter 130. Changing the material density and elasticity of catheter 130 will affect the ultrasonic kinetic energy of the ultrasonic waves imparted within a lumen of catheter 130. Intrinsic material density/elasticity combinations of catheter 130 that result in lower intraluminal ultrasonic kinetic energy may be compensated for by an increase in the power generator.

Additionally or alternatively, modulation of the output frequency, including frequency sweep, square wave frequencies, and pulsed frequencies may be used in order to accommodate various catheters 130 and impart ultrasonic kinetic energy within the catheter lumen. Upon reading this disclosure, one of ordinary skill in the art will understand that other types of frequency output modulation can be used without departing from the spirit of the invention disclosed herein. Reducing the volume of containment (based on slots 124 and submerging walls 128) within the fluid could mediate a higher ultrasonic power density.

Ultrasonication apparatus 100 may also include a handle 140. Handle 140 may be attached and/or coupled to the ultrasonication apparatus 100 at, e.g., the transducer 110 and/or chamber 120. In one embodiment, handle 140 is configured to be gripped by a user's hand, thereby enabling ultrasonication apparatus 100 to be handheld. In another embodiment, ultrasonication apparatus 100 may be moved along contiguous segments of the catheter 130 without causing damage to the catheter 130, itself, thereby facilitating the reduction or elimination of obstructions in long segments of catheter 130.

Desirably, ultrasonication apparatus 100 is configured such that the ultrasonic waves from the transducer 110 reduce and/or eliminate obstructions within catheter 130. Ultrasonication apparatus 100, or features thereof, may advantageously be modified to optimize reduction or elimination of obstructions within the catheter 130, e.g., by increasing the intensity of the cavitation induced by the ultrasonic waves. The desired intensity of the cavitation may depend on the type of obstruction within catheter 130, such as, e.g., one or more of bodily excrement and cellular products.

Attributes of the catheter system (e.g., catheter 130) or the substance therein (e.g. the obstructions, bodily excrement, and/or cellular products) may affect the cavitation produced by ultrasonication apparatus 100, including, e.g., the viscosity, concentration of dissolved gas, pressure, and temperature of the fluid/obstruction within the catheter system. For example, viscosity is correlated to the cavitation intensity. The viscosity of a formed blood clot, e.g., is higher than non-coagulated blood. Thus, adjustments may be made in the design to optimize cavitation. Concentration of dissolved gas in the liquid is also inversely correlated to the cavitation intensity. The less gas is dissolved in the liquid, the more intense the cavitation process is. If external pressure is increased, a greater ultrasonic energy is required to overcome the liquid's intermolecular forces or induce cavitation. Additionally, when holding the power constant for the transducer 110, increases in temperature decrease ultrasonic cavitation.

Without being limited to any theory, the Inventors' believe that transient cavitation serves to promote solid disruption (e.g., of the obstruction) within the liquid substance within the catheter 130, thereby increasing the surface area of the solid in contact with the liquid. Cavitation bubbles in a liquid may be created when the minimum intermolecular distance required to maintain the liquid are overcome by negative pressure induced by ultrasonic frequencies.

Figure 4:
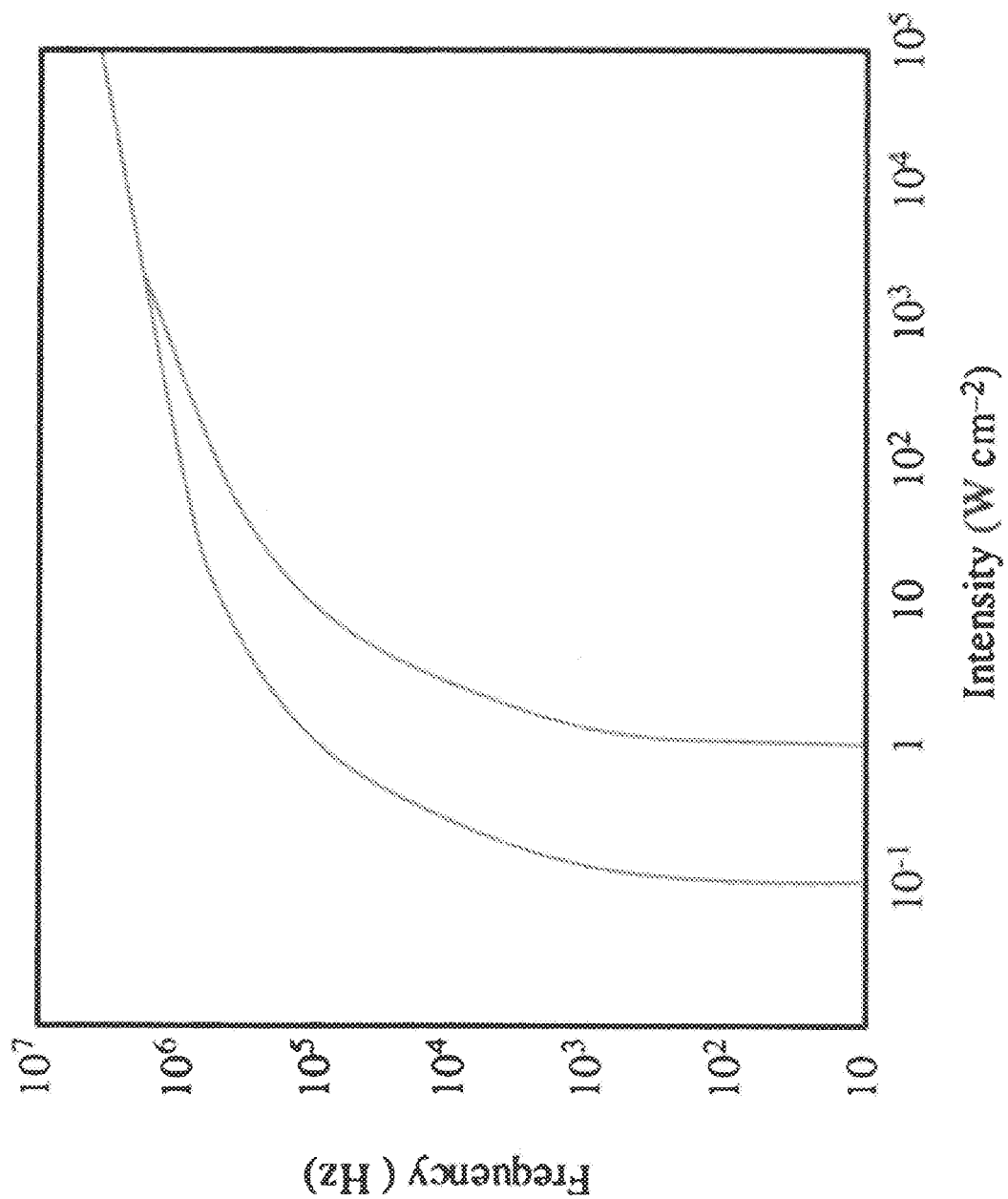
FIG. 4 is a graph illustrating the inverse correlation between ultrasonic frequency and cavitation intensity in accordance with aspects of the present invention.

Accordingly, ultrasonication apparatus 100 may, advantageously, be modified to increase or decrease cavitation produced by ultrasonication apparatus 100. Preferably, the transducer 110 may be configured to produce varying ultrasonic frequencies and/or power to adjust the intensity of cavitation. As depicted in FIG. 4, ultrasonic frequency is inversely correlated to the cavitation intensity. Higher frequencies on the order of megahertz (MHz) result in a lower cavitation intensity. In order to utilize higher frequencies, the intensity of applied sound must be increased to ensure that cavitation occurs. Preferably, the ultrasonic waves are on the order of kilohertz.

Ultrasonic power or amplitude is positively correlated to the cavitation intensity. However, when the power is substantially over the threshold for cavitation, the intensity of cavitation saturates. Preferably, if ultrasonication apparatus 100 is geared toward use on a viscous bodily fluid, then the power and/or frequency should be increased to optimize cavitation.

Figure 5:
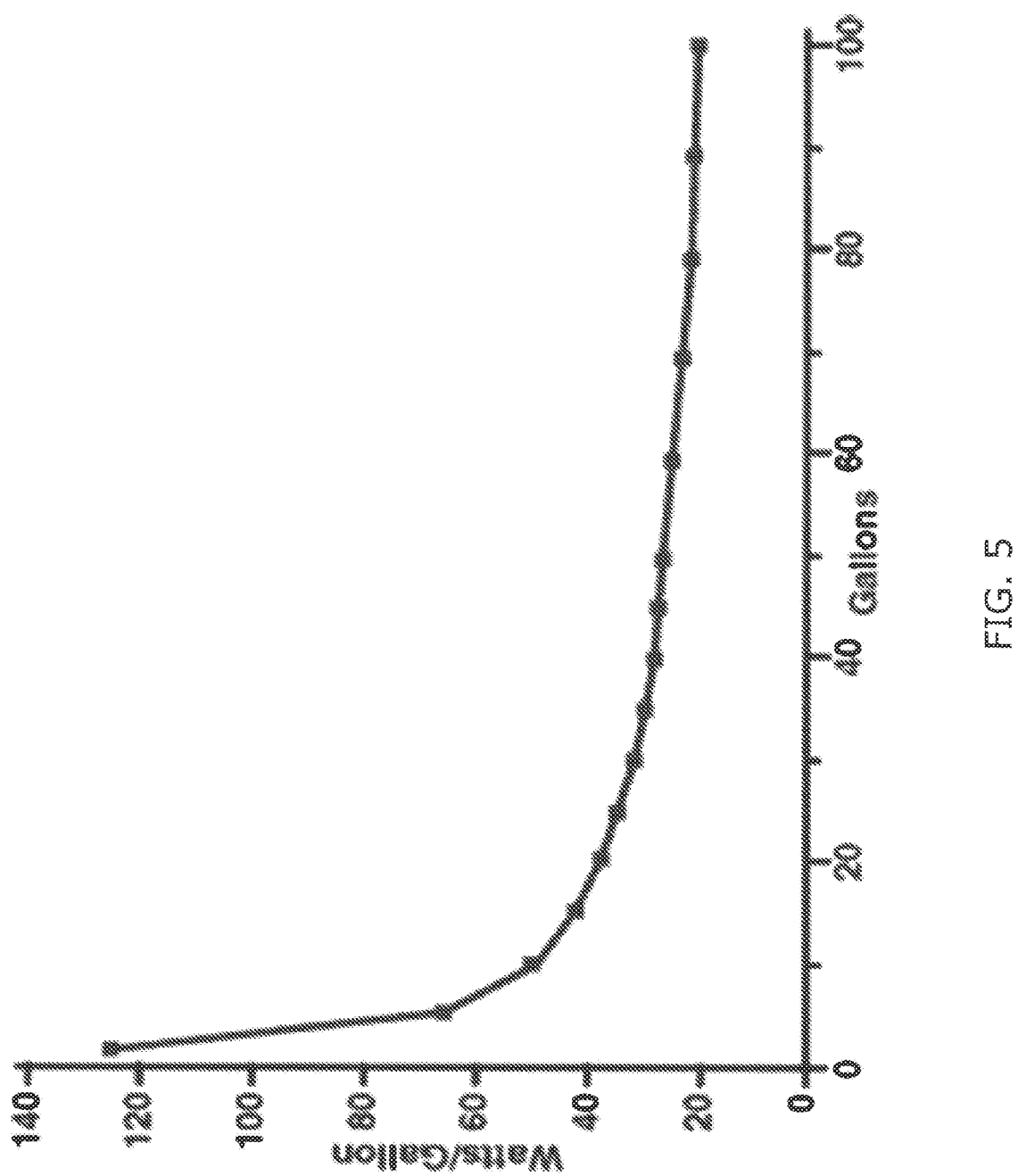
FIG. 5 is a graph illustrating the inverse correlation between the size of the chamber and the ultrasonic power density according to aspects of the present invention.

The ultrasonic power and/or frequency may also be adjusted to the size of the chamber 120. For example, as illustrated in FIG. 5, the ultrasonic power density is inversely correlated to the container size. Thus, the smaller the tank size is, the higher power density (Watts/unit volume) to achieve the same level of ultrasonic cleaning performance.

Additionally or alternatively, the chamber 120 and the fluid contained therein may be modified to adjust the cavitation intensity. Because ultrasonic waves produced by transducer 110 travel through the material of the chamber 120, the fluid within chamber 120, the material of catheter 130, then into the substance (e.g., the obstruction) within the catheter 130, the energy of the ultrasonic waves inside the catheter 130 may be lower and/or altered by the intrinsic properties of the materials that the ultrasonic waves pass through. Thus, employing materials configured to facilitate travel of sound at high speeds may be desired. In one embodiment, the chamber 120 is formed of a material that sound travels there through at 2000 m/s or greater. Preferably, materials for chamber 120 include, e.g., aluminum, which is similar to that of ultrasound gel and permits sound to travel at approximately 5100 m/s; rubber, which permits sound to travel up to 1600 m/s; polyethylene, which enables sound to travel at 2000-2500 m/s; and acrylic, which enables sound to travel at approximately 2730 m/s. In one embodiment, chamber 120 is formed of polycarbonate having a thickness of ¼ inch. Sound may travel through polycarbonate at speeds of 2000-2400 m/s.

Additionally or alternatively, the fluid within chamber 120 may also be changed. The uniform compressibility (bulk modulus) and density of the fluid affect the speed at which sound propagates in a fluid. Sound attenuation within a fluid is dictated by Stokes' Law, whereby the rate of amplitude decrease is inversely proportion to the sound velocity to the third power and the density of the fluid and proportional to the dynamic viscosity of the fluid and the frequency of sound to the second power. Based on these concepts, one of ordinary skill in the art will understand that a number of different fluids are suitable for use within chamber 120. In one embodiment, the fluid contained by the chamber 120 is a water-based solution. In another embodiment, the fluid contained by chamber 120 is a non-water based solution, such as solutions based on, e.g., ethylene glycol, which enables sound to travel at 1600-1700 m/s; glycerol, which enables sound to travel at 1900-2000 m/s; and hypertonic saline (i.e. 3.5% NaCl), which enables sound to travel at 1500-1600 m/s. In a further embodiment, the fluid contained by chamber 120 has a gel formation. The fluid may form a gel that flows under steady state, is a thixotropic fluid that flows under agitation or kinetic motion, or is a dilatant fluid that thickens upon agitation or kinetic motion. In one embodiment, the fluid is an ultrasound gel, which permits sound to travel at approximately 5100 m/s (as mentioned above). In another embodiment, the fluid is a gas (e.g., air). One of skill in the art would readily recognize suitable fluids having a gel formation based on the disclosure provided herein.

Figure 6:
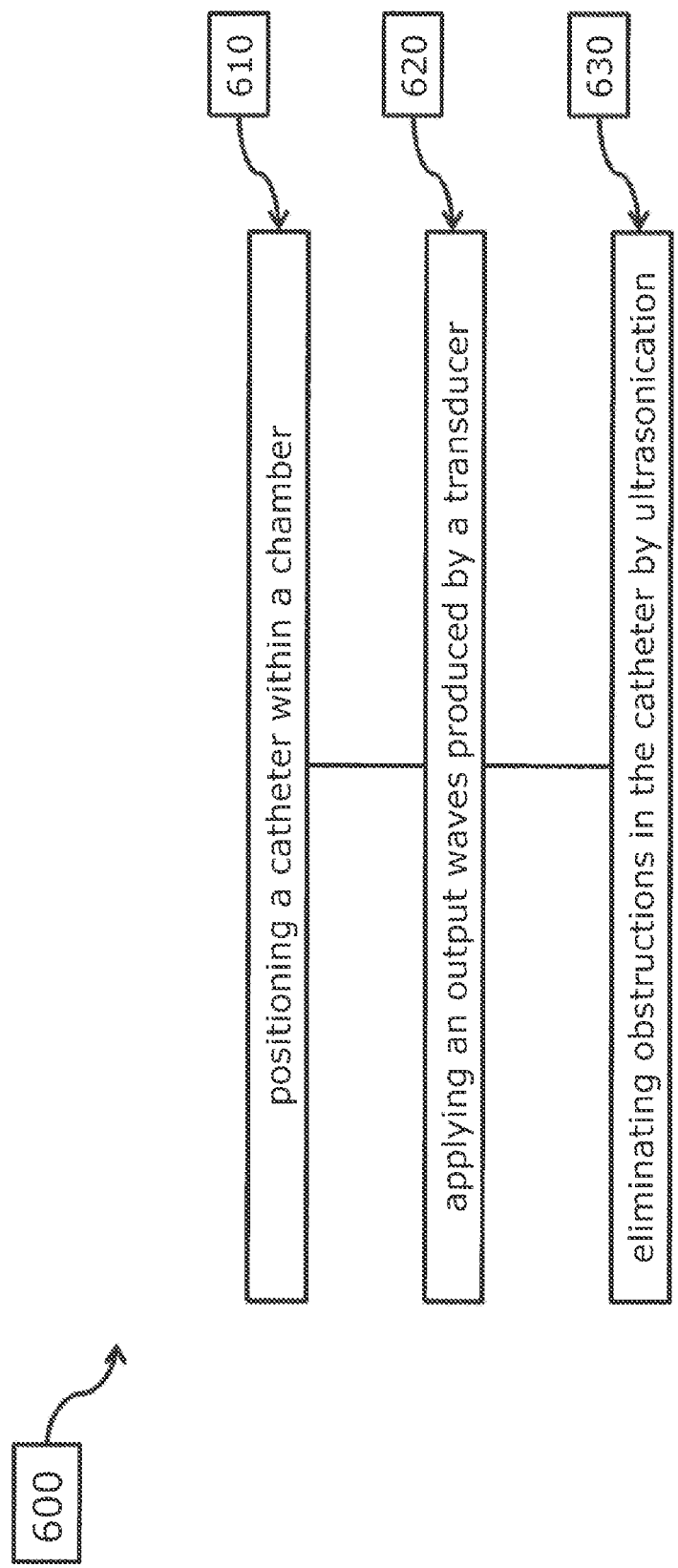
FIG. 6 is a schematic depicting a first method for improving catheter function by ultrasonication in accordance with aspects of the present invention.
Figure 7A:
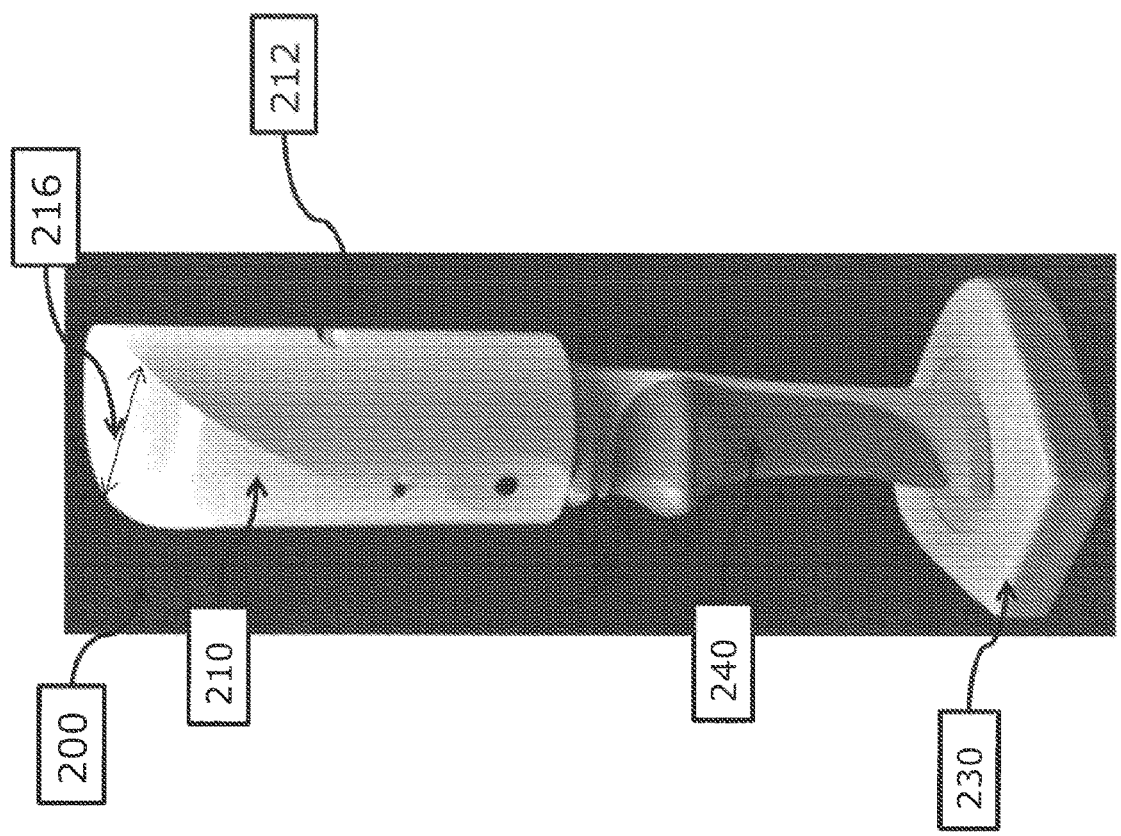
FIGS. 7A-7B are perspective front and back views of a second embodiment of an ultrasonication apparatus for improving catheter function according to aspects of the present invention.
Figure 7B:
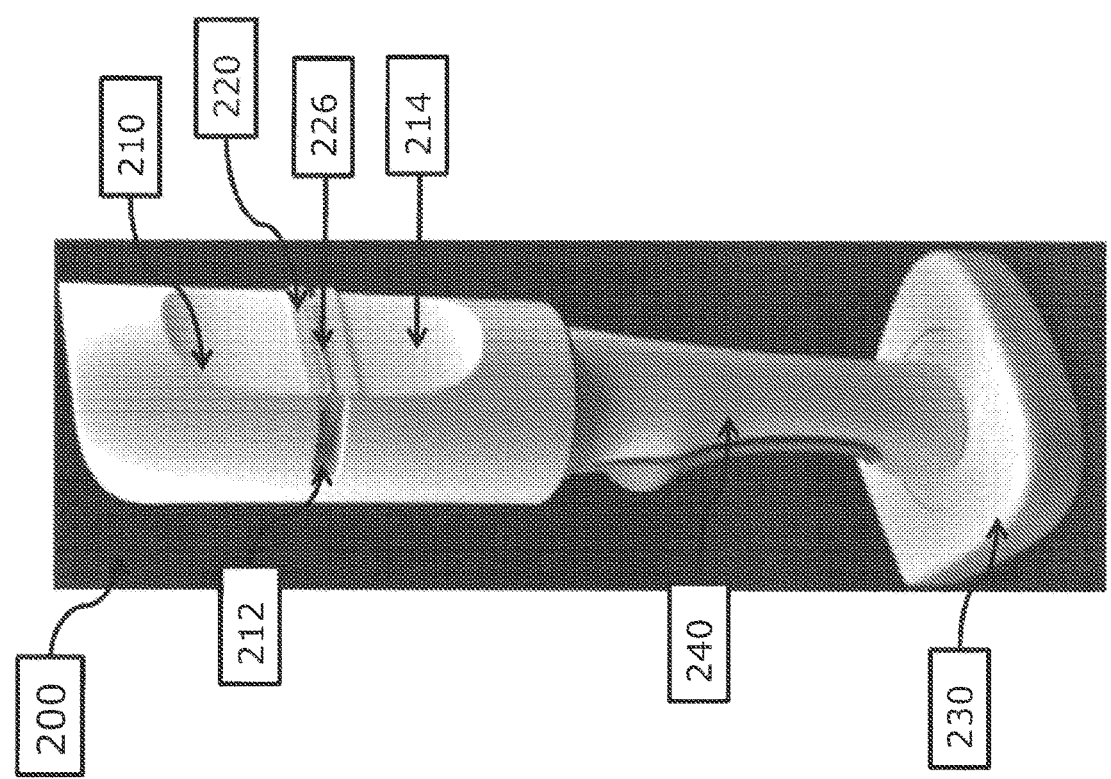

FIG. 6 depicts an embodiment of a method 600 for improving catheter function by ultrasonication in accordance with aspects of the present invention.

In step 610, the catheter 130 is positioned within the chamber 120, which is configured to contain a fluid. The catheter 130 may be inserted into chamber 120, e.g., through passage 122 or by positioning cover 126 in an open position and inserting catheter 130 through the top portion of chamber 120. In one embodiment, cover 126 includes two submerging walls 123a and 128b that contact and position catheter 130 upon moving cover 126 towards a closed position.

In step 620, ultrasonic waves produced by transducer 110 are applied to the segment of catheter 130 positioned within the chamber 120. Preferably, the applied ultrasonic waves are modified by a sweep function that adjusts the frequency of the ultrasonic waves for variations of 5% or less. In one embodiment, the applied ultrasonic waves are modified by a sweep function configured to produce a square wave function. In another embodiment, the applied ultrasonic waves are pulsed.

In step 630, the obstruction in the catheter 130 is eliminated by ultrasonication produced by the ultrasonic waves of the transducer 110. Additionally or alternatively, the ultrasonic waves may be applied to pre-emptively reduce the likelihood of an obstruction occurring within the segment of the catheter 130 receiving the ultrasonic waves. Elimination of the obstruction may further include draining the obstruction outside of the body by way of, e.g., positioning the segment of the catheter 130 receiving the ultrasonic waves at a lower elevation than a proximal segment of the catheter 130 (e.g. the catheter 130 segment entering the patient) and/or by positioning a distal segment of the catheter 130 (e.g. the discarding outlet of the catheter 130) at a lower elevation than the segment of the catheter 130 receiving the ultrasonic waves.

FIGS. 7A, 73, and 9-10B illustrate an additional embodiment of an ultrasonication apparatus 200 for improving catheter function. Ultrasonication apparatus 200 may not utilize a chamber containing a fluid for the ultrasonication of a catheter, but instead may transfer ultrasonic waves to the catheter 130 directly or indirectly through a receptacle 212. As a general overview, ultrasonication apparatuses 200 includes a transducer 210 and a clip 220 adapted to transfer ultrasonic waves to a catheter 130.

Transducer 210 has a receptacle 212 that extends inwardly from a face surface 214 of ultrasonication apparatus 200 to, e.g., a middle region of ultrasonication apparatus 200, thereby forming a channel to receive clip 220 or catheter 130. Preferably, receptacle 212 is accessible along the entire length direction 216 of receptacle 212, such that a segment of catheter 130 may be inserted into receptacle 212 in a radial direction with respect to the segment of catheter 130 (e.g., in a direction that is perpendicular to an axial direction of the segment of catheter 130).

Clip 220 is adapted to be positioned within receptacle 212. Clip 220 may be formed of a material that facilitates the transfer of ultrasonic waves. For example, clip 220 may be formed of plastic, ceramics, metals, composites, or any other advantageous materials. Additionally, a fluid (e.g., a gel) may be disposed on an inner surface of the clip 220 to modify and/or facilitate the ultrasonic waves transferred to catheter 130.

Clip 220 has an open region configured to receive catheter 130. In one embodiment, clip 220 has a U-shaped portion 222 and two leg portions 224 extending from U-shaped portion 222. U-shaped portion 222 may have a protrusion and/or one or more indents for frictionally securing catheter 130 in open region 226 of clip 220, Ultrasonication apparatus 200 may also include a base 230. Base 230 is adapted to receive transducer 210 directly or indirectly (e.g., by way of a handle 240 extending from transducer 210). Base 230 may facilitate or store an electrical charge for transducer 210. In one embodiment, base 230 is coupled to transducer 210 by way of a communication port (e.g., a USB port).

Ultrasonication apparatus 200 may also include a timer 240 configured to activate or deactivate the ultrasonication apparatus 200 after a specified amount of time, such as, e.g., after 5 minutes, 10 minutes, 20 minutes, 40 minutes, 60 minutes, etc. Although timer 240 is located in base 230 in the embodiment illustrated in FIG. 9, timer 240 may be attached and/or coupled to other locations of ultrasonication apparatus 200.

Figure 8B:
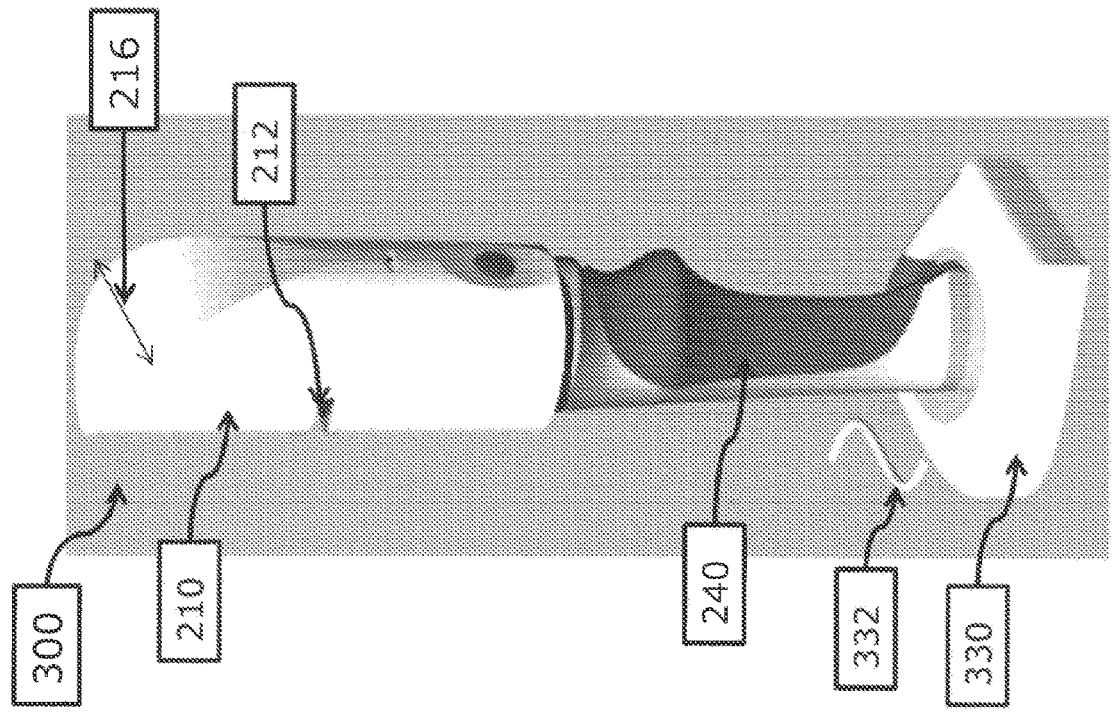
FIGS. 8A-8B are perspective front and back views of a third embodiment of an ultrasonication apparatus for improving catheter function according to aspects of the present invention.
Figure 8A:
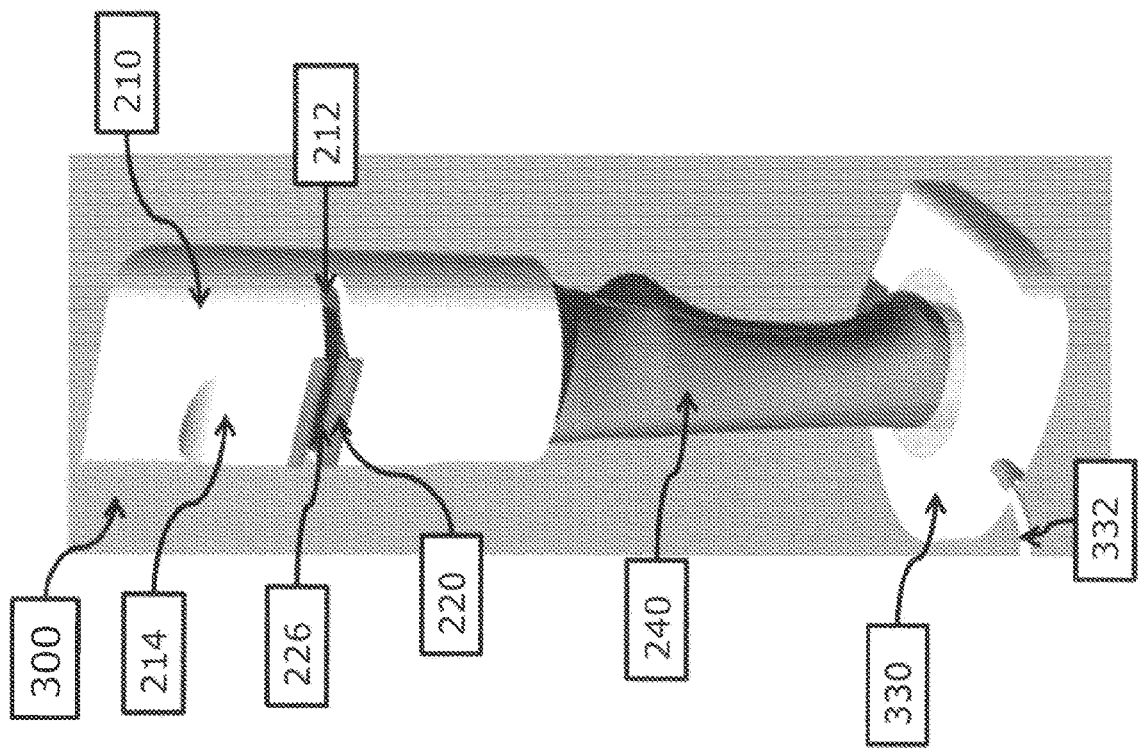
Figure 9:
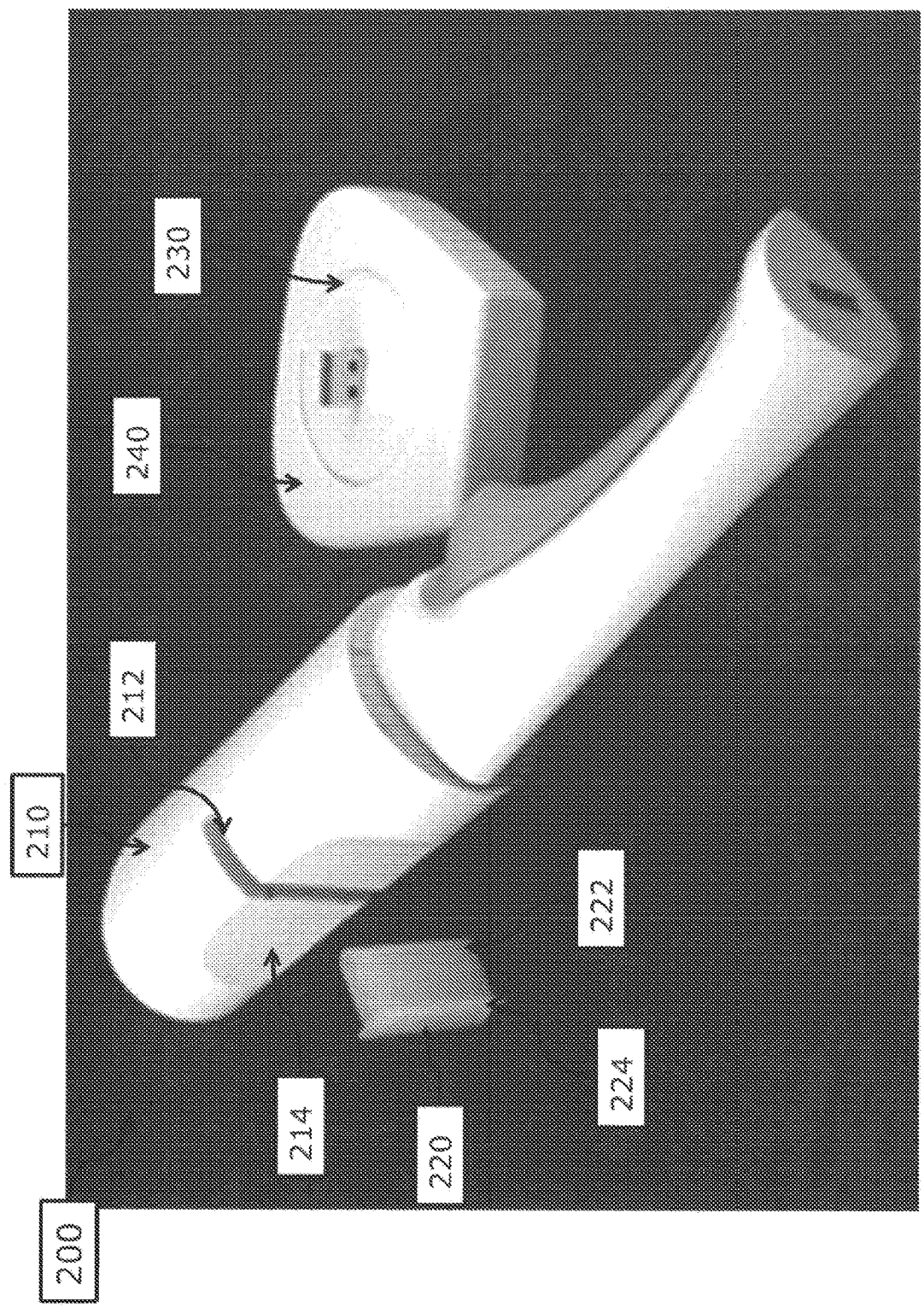
FIG. 9 is a perspective view of the ultrasonication apparatus of FIG. 7A in a disassembled configuration.
Figure 10B:
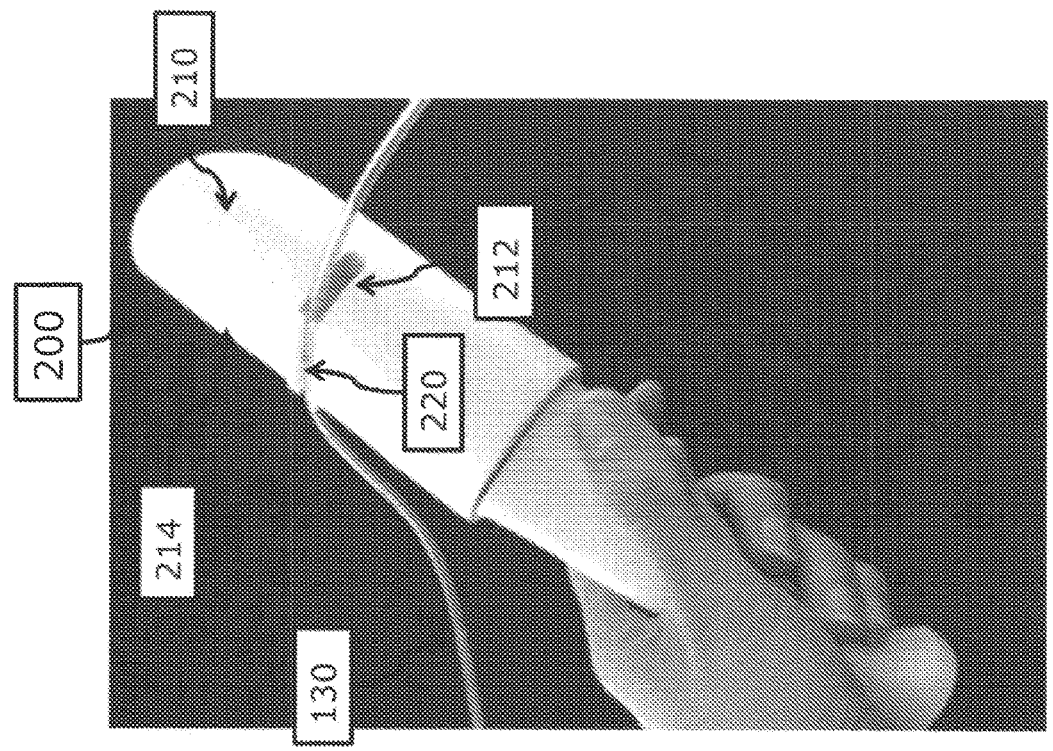
FIGS. 10A and 10B are perspective views of the ultrasonication apparatus of FIG. 7A with a catheter positioned in the receptacle of the ultrasonication apparatus.
Figure 10A:
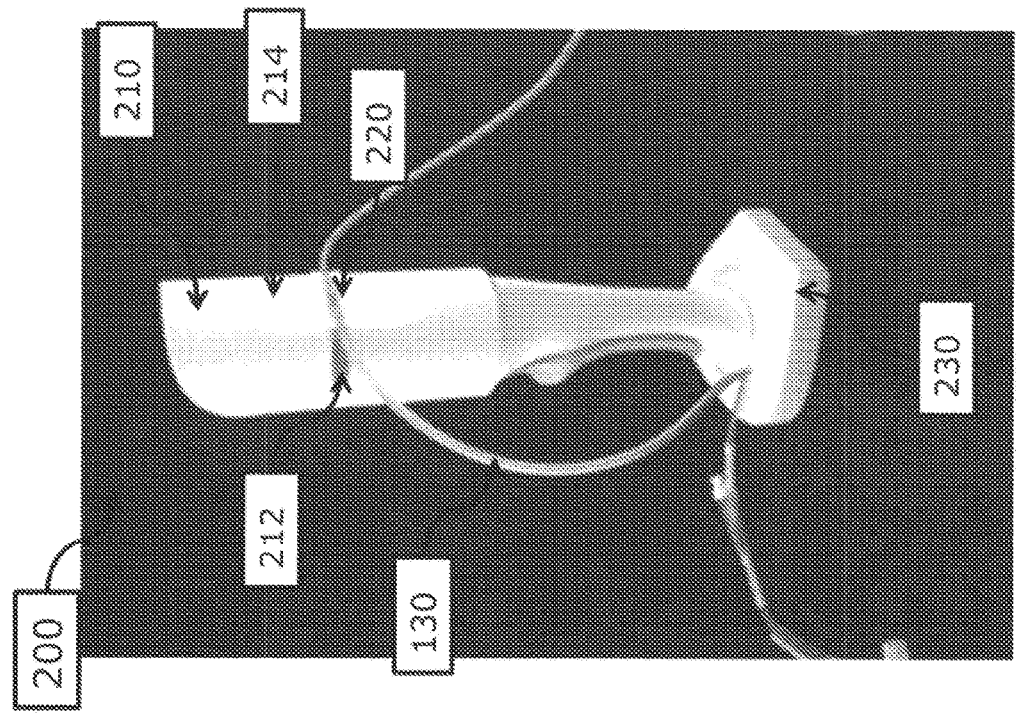

FIG. 8 illustrates another embodiment of an ultrasonication apparatus 300 for improving catheter function. Ultrasonication apparatus 300 is similar to ultrasonication apparatus 200 and, thus, includes several features discussed with reference to ultrasonication apparatus 200. In one embodiment, ultrasonication apparatus 300 includes a base 330 that is connected to a power outlet by way of an electrical cord 332.

Figure 11:
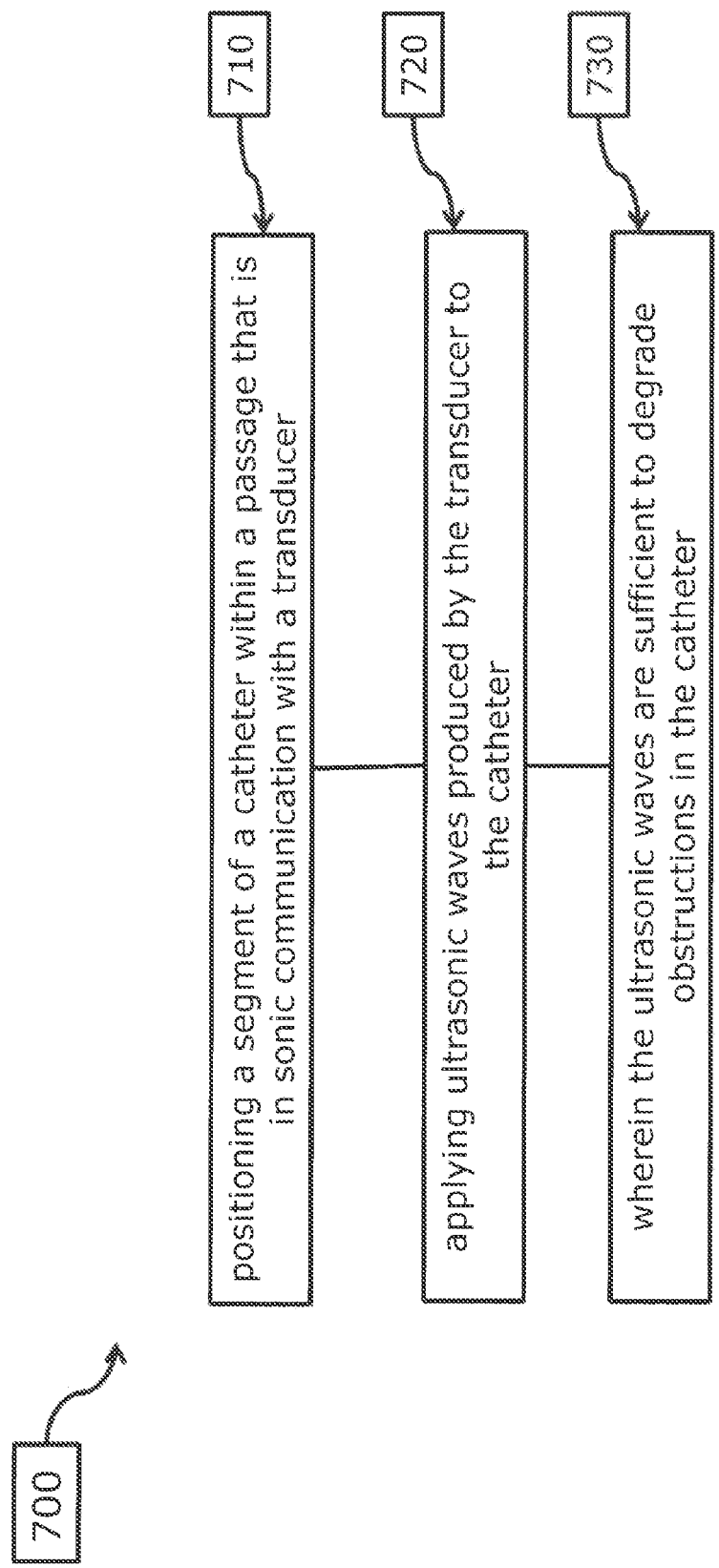
FIG. 11 is a schematic depicting a second method for improving catheter function by ultrasonication in accordance with aspects of the present invention.

FIG. 11 depicts an embodiment of a method 700 for improving catheter function by ultrasonication in accordance with aspects of the present invention.

In step 710, a segment of a catheter is positioned within a receptacle that is in sonic communication with a transducer. The segment of the catheter may be in direct contact with the walls of the receptacle or in indirect contact with the walls of the receptacle, e.g., by way of a clip, to receive ultrasonic waves from the transducer. In one embodiment, a fluid (e.g., a gel) is applied to an inner surface of an open region of the clip and/or inner walls of the receptacle.

In step 720, ultrasonic waves produced by the transducer are applied to the segment of the catheter positioned within the receptacle. Preferably, the applied ultrasonic waves are modified by a sweep function that adjusts the frequency of the ultrasonic waves for variations of 5% or less. In one embodiment, the applied ultrasonic waves are modified by a sweep function configured to produce a square wave function. In another embodiment, the applied ultrasonic waves are pulsed.

In step 730, the obstruction in the catheter is degraded and/or eliminated by ultrasonication produced by the ultrasonic waves of the transducer. Additionally or alternatively, the ultrasonic waves may be applied to pre-emptively reduce the likelihood of an obstruction occurring within the segment of the catheter receiving the ultrasonic waves. Elimination of the obstruction may further include draining the obstruction outside of the body by way of, e.g., positioning the segment of the catheter receiving the ultrasonic waves at a lower elevation than a proximal segment of the catheter (e.g. the catheter segment entering the patient) and/or by positioning a distal segment of the catheter (e.g. the discarding outlet of the catheter) at a lower elevation than the segment of the catheter receiving the ultrasonic waves.

EXAMPLE

The following example is a non-limiting embodiment of the present invention, included herein to demonstrate the advantageous results obtained from aspects of the present invention.

A catheter system (produced by Integra LifeSciences Accudrain, Plainsboro Township, N.J.) similar to those used for external ventricular drains was unobstructed using a method and apparatus in accordance with aspects of the present invention.

To produce the obstructed catheter, the catheter system was first primed with normal saline, and then human blood was instilled to create an obstruction in the lumen of the drain. The catheter system was tested to determine that the obstruction inhibited flow from the catheter tip, which in theory, but not during testing, would be inside the cerebral ventricles to the external reservoir.

To remove the obstruction from the catheter system, the clotted segment of the catheter was placed within an ultrasonication apparatus in accordance with aspects of the present invention. Ultrasonication resulted in a rapid non-invasive clot lysis and flow within the length of the catheter segment leading to the reservoir. At the end of the procedure, the catheter was completely intact and patency was established. The clotted blood drained into an external reservoir. This result was reproducible.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An ultrasonication apparatus for improving catheter function comprising:
   a transducer configured to produce ultrasonic waves; and
   a chamber configured to contain at least one of a water based solution and a gel and adapted to receive the ultrasonic waves from the transducer, the chamber including a slot along a bottom of the chamber and,
   a cover moveable from an open position to a closed position, the cover including a first opening, a second opening, and a submerging wall extending from the cover towards the bottom of the chamber,
   wherein a passage is defined between the first opening and the second opening with the slot therebetween, the passage configured to receive a catheter therein extending between the first opening and the second opening, and wherein the submerging wall is configured to position the catheter within the slot as the cover moves from an open position to a closed condition;
   wherein the ultrasonic waves are configured to eliminate at least one obstruction in the catheter.

2. The ultrasonication apparatus of claim 1, wherein the ultrasonic waves have a frequency of approximately 40 kHz, or 60 kHz.

3. The ultrasonication apparatus of claim 1, wherein the chamber is formed of a material that sound travels therethrough at 2000 m/s or greater.

4. The ultrasonication apparatus of claim 1, wherein the chamber is formed of polycarbonate.

5. The ultrasonication apparatus of claim 1, wherein the at least one obstruction in the catheter is one or more of bodily excrement and cellular products.

6. The ultrasonication apparatus of claim 1, wherein the transducer employs a sweep function to modify the frequency of the ultrasonic waves.

7. The ultrasonication apparatus of claim 1, wherein a fluid comprising at least one of a water based solution and a gel is disposed in the chamber, and wherein the fluid does not flow under room temperature and pressure.

8. The ultrasonication apparatus of claim 1, wherein the apparatus is handheld.

9. The ultrasonication apparatus of claim 8, further comprising a handle coupled to at least one of the transducer and the chamber.

10. The ultrasonication apparatus of claim 1, wherein the apparatus is configured to be moved along contiguous segments of the catheter.

11. The ultrasonication apparatus of claim 1, wherein the transducer is configured to pulse the ultrasonic waves.

12. The ultrasonication apparatus of claim 1, wherein the transducer is configured to produce ultrasonic waves having a square waveform.

* * * * *